(12) United States Patent
King

(10) Patent No.: US 7,175,844 B2
(45) Date of Patent: Feb. 13, 2007

(54) METHODS OF MODULATING FIBROSIS

(75) Inventor: George L. King, Dover, MA (US)

(73) Assignee: Joslin Diabetes Center, Inc., Boston, MA (US)

(*) Notice: Subject to any disclaimer, the term of this patent is extended or adjusted under 35 U.S.C. 154(b) by 377 days.

(21) Appl. No.: 09/907,045

(22) Filed: Jul. 17, 2001

(65) Prior Publication Data

US 2002/0086013 A1 Jul. 4, 2002

Related U.S. Application Data

(60) Provisional application No. 60/219,244, filed on Jul. 18, 2000.

(51) Int. Cl.
*A61K 39/395* (2006.01)
*A61K 39/00* (2006.01)

(52) U.S. Cl. ............... 424/130.1; 424/133.1; 424/141.1; 424/143.1; 424/145.1

(58) Field of Classification Search .......... 514/2; 530/387.1
See application file for complete search history.

(56) References Cited

U.S. PATENT DOCUMENTS

| | | | |
|---|---|---|---|
| 6,001,622 A | 12/1999 | Dedhar et al. | |
| 6,100,090 A | 8/2000 | Monia et al. | |
| 6,410,322 B1 * | 6/2002 | Robinson | 435/375 |
| 6,455,283 B1 * | 9/2002 | Ferrara et al. | |
| 6,620,784 B1 * | 9/2003 | Ferrara et al. | 514/12 |
| 6,734,285 B2 * | 5/2004 | Hu et al. | 530/350 |

FOREIGN PATENT DOCUMENTS

| | | |
|---|---|---|
| WO | WO 94/10202 | 5/1994 |
| WO | WO 97/34920 | 9/1997 |
| WO | WO 00/13706 | 3/2000 |

OTHER PUBLICATIONS

Jiang et al., "Phosphatidylinositol 3-Kinase signaling mediates . . .", Feb. 2000, Proc.Natl.Acad.Sci., vol. 97, No. 4;1749-1753.
Oikawa et al., "Potent inhibition of angiogenesis by wortmannin . . .", 1996, Eur.J.Pharmacol, vol. 318;93-96.
Snyder et al., "Effects of inhibitors of phosphatidylinositol 3-OH kinase . . .", 1998, abstract, Blood, vol. 92, No. 10, Pt. 1, Suppl. 1;426a-427a.
Abraham et al. (2000) *J. Biol. Chem.* 275, 15220.
Aiello et al. (1998) *Diabetes Care* 21, 143.
Boes et al. (1999) *Endocrinology* 140, 1575.
Chen et al., Oct. (2000) *J Mol Cell Cardiol.* 32(10):1805-19.
Clarkson et al. Sep. (1999) *Curr Opin Nephrol Hypertens.* 8(5):543-8. Review. No abstract available.
Dammeier et al. (1998) *J. Biol. Chem.* 273, 18185-18190.
Dammeier et al. Aug. (1998) *Int J Biochem Cell Biol.*30(8):909-22.
Firestein (1999) *J. Clin. Invest.* 103, 3-4.
Frazier et al. (1996) *J. Invest. Dermatol.* 107, 404.
Haustein et al. Jul (1998)*J Eur Acad Dermatol Venereol.* 11(1):1-8. Review.
Holmes et al. Apr. (2001)*J Biol Chem.* 276(14):10594-601.
Igarashi et al. (1996) *J. Invest. Dermatol.* 106, 729-733.
Ito et al. Mar (2001)*J Am Soc Nephrol.*12(3):472-84.
Kireeva et al. (1997) *Exp. Cell Res.* 233, 63.
Klagsbrun & D'Amore, (1991) *Annu. Rev. Physiol.* 53, 217.
Lopez et al. (1996) *Invest. Ophthalmol. &Visual Sci.* 37, 855.
Mola et al. Jul (1999) *Ann. Surg.*230(1):63-71.
Mori et al. Oct (1999) J Cell Physiol.181(1):153-9.
Murphy et al. (1999) *J. Biol. Chem.* 274, 5830-5834.
Pendurthi et al. (2000) *J. Biol. Chem.* 275, 14632-14641.
Petrova et al. (1999) *Exp. Cell Res.* 253, 117-130.
Ricupero et al. (2000) *J. Biol. Chem.* 275, 12475-12480.
Sato et al. Jan (2000) *J Rheumatol.*27(1):149-54.
Lasky et al., "Connective tissue growth factor mRNA expression . . . ", 1998, Amer. Physiol. Soc., p. L365-371.
King, "Cell biology as an approach to the study of the vascular complications of diabetes," *Metabolism*, 34(12 Suppl. 1):17-22, Abstract only (1985).
King et al., "Regulation of vascular Permeability in Cell Culture," *Diabetes*, 36:1460-1467 (1987).
Rauniyar et al., "Differential Effects of Bactericidal/Permeability-Increasing Protein (BPI) Analogues on Retinal Neovascularization and Retinal Pericyte Growth," *Invest. Ophthalmol. Vis. Sci.*, 43(2):503-509 (2002).
Suzuma et al., "Vascular Endothelial Growth Factor Induces Expression of Connective Tissue Growth Factor via FDR, Flt1, and Phosphatidylinositol 3-Kinase-Akt-dependent Pathways in Retinal Vascular Cells," *J. Biol Chem.*, 275(52):40725-40731 (2000).
Takagi et al., "Adenosine Mediates Hypoxic Induction of Vascular Endothelial Growth Factor in Retinal Pericytes and Endothelial Cells," *Invest. Ophthalmol. Vis. Sci.*, 37(11):2165-2176 (1996).
Takagi et al., "Identification and characterization of vascular endothelial growth factor receptor (Flt) in bovine retinal pericytes," *Diabetes*, 45(8):1016-1023, Abstract only (1996).
Kim et al., "Inhibition of vascular endothelial growth factor-induced angiogenesis suppresses tumor growth *in vivo*," *Nature*, 362:841-844 (1993).
Hamada et al., "Anti-vascular endothelial growth factor gene therapy attenuates lung injury and fibrosis in mice." J. Immunol. 175(2):1224-1231 (2005).
Kalluri and Sukhatme, "Fibrosis and angiogenesis." Curr. Opin. Nephrol. Hypertens. 9(4):413-8 (2000).
Medford et al., "VEGF in idiopathic ILD." Thorax 60(4):353 (2005).
Richter et al., "VEGF levels in pulmonary fibrosis." Thorax 60(2):171 (2005).
Rojkind and Greenwel, "Animal models of liver fibrosis." in *Animal Models in Liver Research*, (Cornelius, Ed.), Adv. Vet. Sci. Comp. Med. (37):333-355 (1993).
Saleem et al., "Author's Reply." Thorax 60(4):353-354 (2005).
Simler et al., "Angiogenic cytokines in patients with idiopathic interstitial pneumonia." Thorax 59:581-585 (2004).
Yoshiji et al., "Vascular endothelial growth factor and receptor interaction is a prerequisite for murine hepatic fibrogenesis." Gut 52:1347-1354 (2003).
Babic et al., "Fisp12/mouse connective tissue growth factor mediates endothelial cell adhesion . . . " Mol. and Cell. Biol. 19:2958-2966, 1999.
Suzuma et al., "Vascular endothelial growth factor induces expression of connective tissue growth . . . " J. of Biol. Chem. 275:40725-40731, 2000.
Wunderlich et al., "Regulation of connective tissue growth factor gene expression in retinal vascular endothelial . . . " Graefe's Archive for Clinical & Exp. Ophthalmology 238:910-915, 2000.

* cited by examiner

*Primary Examiner*—Robert S. Landsman
(74) *Attorney, Agent, or Firm*—Fish & Richardson P.C.

(57) ABSTRACT

The invention features methods of modulating fibrosis and/or angiogenesis by inhibiting components of the VEGF signaling pathway. The methods are useful in the treatment of fibrotic and or angiogenesis related disorders.

26 Claims, No Drawings

METHODS OF MODULATING FIBROSIS

RELATED APPLICATIONS

This application claims the benefit of U.S. Provisional application No. 60/219,244, filed on Jul. 18, 2000, the contents of which are incorporated herein by reference in their entirety.

GOVERNMENT RIGHTS

This invention was made with support from the U.S. government under grant number NIH EY 5110 awarded by the National Institutes of Health. The government has certain rights in the invention.

BACKGROUND

Angiogenesis and fibrosis are key components in development, growth, wound healing, and regeneration (Klagsbrun & D'Amore, (1991) *Annu. Rev. Physiol.* 53, 217–239). In addition, these processes commonly occur together in many disease states where neovascularization is believed to initiate the pathological cascade, including proliferative diabetic retinopathy (Aiello et al. (1998) *Diabetes Care* 21, 143–156), rheumatoid arthritis (Firestein (1999) *J. Clin. Invest.* 103, 3–4), and age-related macular degeneration (Lopez et al. (1996) *Invest. Ophthalmol. & Visual Sci.* 37, 855–868).

Vascular endothelial growth factor (VEGF) is expressed as a family of peptides of 121, 145, 165, 189, and 206 amino acid residues. Its expression is induced by hypoxia and is essential in the vasculogenesis process during development. Several receptors have been shown to mediate the action of VEGF, and most of them belong to the tyrosine kinase receptor family (Petrova et al. (1999) *Exp. Cell Res.* 253, 117–130). Upon the binding of VEGF to its receptors, multiple signaling cascades are activated, including the tyrosine phosphorylation of phospholipase Cγ, elevation of intracellular calcium and diacylglycerol, activation of protein kinase C (PKC), and extracellular signal-regulated kinase (MAPK/ERK) for endothelial cell proliferation. In addition, VEGF also stimulates activation of phosphatidylinositol (PI) 3-kinase leading to Akt/PKB activation and possibly enhancing endothelial cell survival.

Connective tissue growth factor (CTGF) is a potent and ubiquitously expressed growth factor that has been shown to play a unique role in fibroblast proliferation, cell adhesion, and the stimulation of extracellular matrix production (Frazier et al. (1996) *J. Invest. Dermatol.* 107, 404–411; Kireeva et al. (1997) *Exp. Cell Res.* 233, 63–77). The 38-kDa protein was originally identified in conditioned medium from human umbilical vein endothelial cells, and the expression was shown to be selectively stimulated by transforming growth factor-β (TGF-β) in cultured fibroblasts. Due to its mitogenic action on fibroblasts and its ability to induce the expression of the extracellular matrix molecules, collagen type I, fibronectin, and integrin α5, CTGF is supposed to play an important role in connective tissue cell proliferation and extracellular matrix deposition as one of the mediators of TGF-β. CTGF also seems to be an important player in the pathogenesis of various fibrotic disorders, since it was shown to be overexpressed in scleroderma, keloids, and other fibrotic skin disorders (Igarashi et al. (1996) *J. Invest. Dermatol.* 106, 729–733), as well as in stromal rich mammary tumors, and in advanced atherosclerotic lesions. Recently, the integrin α5β3 has been reported to serve as a receptor on endothelial cells for CTGF-mediated endothelial cell adhesion, migration, and angiogenesis (Babic et al. (1999) *Mol. Cell. Biol.* 19, 2958–2966).

Besides TGF-β, the expression of CTGF is reported to be regulated by dexamethasone in BALB/c 3T3 cells, high glucose in human mesangial cells, kinin in human embryonic fibroblasts, factor VIIa, and thrombin in WI-38 fibroblasts, tumor necrosis factor α in human skin fibroblast, and cAMP in bovine endothelial cells (Dammeier et al. (1998) *J. Biol. Chem.* 273, 18185–18190; Murphy et al. (1999) *J. Biol. Chem.* 274, 5830–5834; Ricupero et al. (2000) *J. Biol. Chem.* 275, 12475–12480; Pendurthi et al. (2000) *J. Biol. Chem.* 275, 14632–14641; Abraham et al. (2000) *J. Biol. Chem.* 275, 15220–15225; Boes et al. (1999) *Endocrinology* 140, 1575–1580).

SUMMARY

The invention is based, in part, on the discovery that VEGF can regulate connective tissue growth factor (CTGF), e.g., through the PI3 Kinase-Akt pathway. CTGF is a potent diffusible growth factor which regulates extracellular matrix deposition and connective tissue cell proliferation. CTGF is a potent activator of fibrosis, angiogenesis, and extracellular matrix production. Modulation of the levels of CTGF via the VEGF pathway, e.g., by modulation of a VEGF activity, e.g., a VEGF signaling activity, e.g., a VEGF receptor (VEGFR) activity, e.g., KDR/flk1, Flt1, Flt 4, neuropilin-1 (NP-1), tie, or tie2 activity; modulation of PI3-kinase; or modulation of Akt can thereby stimulate or alternatively reduce fibrosis and/or angiogenesis. Accordingly, one aspect of the invention features methods of modulating fibrosis. Another aspect features methods of modulating angiogenesis.

In one aspect, the invention features a method of decreasing fibrosis in a tissue, e.g., a skin, lung, retinal, renal, cardiac, or liver tissue of a subject, e.g., a human or non-human animal, by decreasing CTGF activity or expression. CTGF activity or expression is decreased by decreasing a VEGF signaling activity. In a preferred embodiment, the method includes identifying a subject in need of decreased fibrosis, e.g., a subject having a fibrotic disorder, e.g., a disorder described herein.

In a preferred embodiment, VEGF signaling is decreased by administering an agent that inhibits a component of the VEGF signal transduction pathway, e.g., an agent that decreases VEGF activity, decreases VEGF receptor (VEGFR) activity, e.g., KDR/flk1, Flt1, Flt4, NP-1, tie, or tie2 activity; decreases PI3-kinase activity; decreases an Akt activity; decreases an Erk activity.

In a preferred embodiment, KDR, Flt-4, Flt-1 or neuropilin activity is decreased.

In a preferred embodiment, the subject has a disorder related to unwanted or excessive fibrosis. In some embodiments, fibrosis is exhibited in, e.g., skin, liver, kidney, cardiac, or lung tissue. The disorder can be caused by scarring, e.g., keloid formation. Examples of other disorders related to unwanted or excessive fibrosis include, but are not limited to, scleroderma (e.g., morphea, generalized morphea, linear scleroderma); keloids; kidney fibrosis, e.g., glomerular sclerosis or renal tubulointerstitial fibrosis; pulmonary fibrosis, e.g., diffuse interstitial pulmonary fibrosis; cardiac fibrosis; chemotherapy/radiation induced lung fibrosis; pancreatitis; a disease of the kidney, e.g., glomerular sclerosis, renal tubulointerstitial fibrosis, or progressive renal disease; atherosclerotic plaques, e.g., restenosis; inflammatory bowel disease; Crohn's disease; arthritic joints, e.g., rheumatoid arthritis; cancer, e.g., invasive breast carcinoma, stromal rich mammary tumors, dermatofibromas, angiolipoma, and angioleiomyoma; hypertrophic scar; nodular fasciitis, eosinophilic fasciitis, dupuytren's contracture; macular degeneration, e.g., age-related macular degeneration; acute ocular neovascularization or diabetic retinopathy; general fibrosis syndrome, characterized by replacement of normal muscle tissue by fibrous tissue in varying degrees; retroperitoneal fibrosis; liver fibrosis; acute fibrosis, e.g., in response to various forms of trauma including accidental injuries, infections, surgery, burns, radiation or chemotherapy treatments; or macular degeneration, e.g., age-related macular degeneration;

The method includes administering an agent which decreases CTGF activity or expression. In a preferred embodiment, the agent is an agent described herein that decreases a VEGF signaling activity.

In a preferred embodiment, CTGF activity or expression is decreased in an endothelial cell.

In a preferred embodiment, CTGF activity or expression is decreased in a pericyte.

An agent which decreases CTGF activity can be one or more of: an agent which decreases the level or activity of VEGF, e.g., an agent which inhibits VEGF interaction with a VEGF receptor (VEGFR), e.g., flt4, flt1, NP-1 tie, tie-2, and/or KDR/flk1; an agent which inhibits VEGF receptor activation; an agent which disrupts a VEGF-VEGFR complex; an agent which inhibits PI3 Kinase activity; an agent that inhibits VEGFR binding to p85, the catalytic subunit of PI3 kinase; an agent which inhibits AKT kinase activity.

In a preferred embodiment, VEGF is inhibited. VEGF can be inhibited by administering an agent which inhibits VEGF gene expression, protein production levels and/or activity. An agent which inhibits VEGF can be one or more of: a VEGF binding protein, e.g., a soluble VEGF binding protein, e.g., the ectodomain of a VEGF-receptor; an antibody that specifically binds to the VEGF protein, e.g., an antibody that disrupts VEGF's ability to bind to its natural cellular target, e.g., disrupts VEGF's ability to bind to a VEGF receptor, e.g., Flt1 (VEGFR1), Flk1/KDR (VEGFR2), NP-1, tie, tie-2, or Flt4 (VEGFR3); an antibody that disrupts the ability of a VEGF receptor to bind to VEGF; an antibody or small molecule which disrupts a complex formed by VEGF and its receptor; a mutated inactive VEGF or fragment which binds to a VEGF receptor but does not activate the receptor; a VEGF nucleic acid molecule which can bind to a cellular VEGF nucleic acid sequence, e.g., mRNA, and inhibit expression of the protein, e.g., an antisense molecule or VEGF ribozyme; an agent which decreases VEGF gene expression, e.g., a small molecule which binds the promoter of VEGF. In another preferred embodiment, VEGF is inhibited by decreasing the level of expression of an endogenous VEGF gene, e.g., by decreasing transcription of the VEGF gene. In a preferred embodiment, transcription of the VEGF gene can be decreased by: altering the regulatory sequences of the endogenous VEGF gene, e.g., by the addition of a negative regulatory sequence (such as a DNA-biding site for a transcriptional repressor), or by the removal of a positive regulatory sequence (such as an enhancer or a DNA-binding site for a transcriptional activator). In another preferred embodiment, the antibody which binds VEGF is a monoclonal antibody, e.g., a humanized chimeric or human monoclonal antibody.

In a preferred embodiment, VEGF interaction with its receptor is inhibited. An agent which inhibits a VEGF receptor, e.g., Flt1 (VEGFR1), Flk1/KDR (VEGFR2), neuropilin-1, tie, tie-2, or Flt4 (VEGFR3), can be one or more of: a VEGF receptor nucleic acid molecule which can bind to a cellular VEGF receptor nucleic acid sequence, e.g., mRNA, and inhibit expression of the protein, e.g., an antisense molecule or VEGF receptor ribozyme; an agent which decreases VEGF receptor gene expression, e.g., a small molecule which binds the promoter of a VEGF receptor. In another preferred embodiment, a VEGF receptor is inhibited by decreasing the level of expression of an endogenous VEGF receptor gene, e.g., by decreasing transcription of an VEGF receptor gene. In a preferred embodiment, transcription of a VEGF receptor gene can be decreased by: altering the regulatory sequences of an endogenous VEGF receptor gene, e.g., by the addition of a negative regulatory sequence (such as a DNA-biding site for a transcriptional repressor), or by the removal of a positive regulatory sequence (such as an enhancer or a DNA binding site for a transcriptional activator); as well as agents described above.

In a preferred embodiment, PI3 kinase is inhibited. An agent which inhibits PI3-kinase activity can be one or more of: a small molecule which inhibits PI3-kinase activity, e.g., LY294002; a protein or peptide that inhibits PI3 kinase activity, e.g., a PI3 kinase binding protein which binds to PI3-kinase but does not activate the enzyme, or a dominant negative form of p85; an antibody that specifically binds to the PI3-kinase protein, e.g., an antibody that disrupts PI3-kinase's catalytic activity or an antibody that disrupts the ability of cellular receptors to activate PI3-kinase; a PI3 kinase nucleic acid molecule which can bind to a cellular PI3 kinase nucleic acid sequence, e.g., mRNA, and inhibit expression of the protein, e.g., an antisense molecule or PI3-kinase ribozyme; an agent which decreases PI3-kinase gene expression, e.g., a small molecule which binds the promoter of PI3-kinase. In another preferred embodiment, PI3-kinase is inhibited by decreasing the level of expression of an endogenous PI3-kinase gene, e.g., by decreasing transcription of the PI3-kinase gene. In a preferred embodiment, transcription of the PI3-kinase gene can be decreased by: altering the regulatory sequences of the endogenous PI3-kinase gene, e.g., by the addition of a negative regulatory sequence (such as a DNA-biding site for a transcriptional repressor), or by the removal of a positive regulatory sequence (such as an enhancer or a DNA-binding site for a transcriptional activator). In another preferred embodiment, PI3-kinase activity is inhibited by a specific small molecule inhibitor, e.g., wortmannin or LY294002.

In another preferred embodiment, AKT kinase is inhibited. An agent which inhibits AKT kinase activity can be one or more of: a specific small molecule which inhibits AKT activity; an AKT binding protein which binds to AKT but does not activate the enzyme; an antibody that specifically binds to the AKT protein, e.g., an antibody that disrupts AKT's catalytic activity or an antibody that disrupts the ability of the AKT PH domain to sense activating second messengers, e.g., phosphoinositides; a mutated inactive AKT or fragment which binds to a AKT receptor but does not activate the receptor; an AKT nucleic acid molecule which can bind to a cellular AKT nucleic acid sequence, e.g., mRNA, and inhibit expression of the protein, e.g., an antisense molecule or AKT ribozyme; an agent which decreases AKT gene expression, e.g., a small molecule which binds the promoter of AKT. In another preferred embodiment, AKT is inhibited by decreasing the level of expression of an endogenous AKT gene, e.g., by decreasing transcription of the AKT gene. In a preferred embodiment, transcription of the AKT gene can be decreased by: altering the regulatory sequences of the endogenous AKT gene, e.g., by the addition of a negative regulatory sequence (such as a DNA-biding site for a transcriptional repressor), or by the removal of a positive regulatory sequence (such as an enhancer or a DNA-binding site for a transcriptional activator).

In one embodiment, increasing a PKC activity, e.g., a PKCα, PKCβ1, PKCβ2, or PKCγ activity, can inhibit PI3 kinase or Akt, thus decreasing CTGF expression or activity. The agent which increases the level of PKC activity can be one or more of the following: a small molecule which stimulates PKC activity, e.g., PMA; a PKC polypeptide or a functional fragment or analog thereof; a nucleotide sequence encoding a PKC polypeptide or functional fragment or analog thereof; an agent which increases PKC nucleic acid expression; e.g., a small molecule which binds to the promoter region of PKC. In a preferred embodiment, PKC levels are increased by administering, e.g., introducing, a nucleotide sequence encoding a PKC polypeptide or functional fragment or analog thereof, into a particular cell, e.g., an endothelial cell, a fibroblast, or a pericyte, in the subject. The nucleotide sequence can be a genome sequence or a cDNA sequence. The nucleotide sequence can include: a PKC coding region; a promoter sequence, e.g., a promoter sequence from a PKC gene or from another gene; an enhancer sequence; untranslated regulatory sequences, e.g., a 5'untranslated region (UTR), e.g., a 5'UTR from a PKC gene or from another gene, a 3'UTR, e.g., a 3'UTR from a PKC gene or from another gene; a polyadenylation site; an insulator sequence. In another preferred embodiment, the level of PKC protein is increased by increasing the level of expression of an endogenous PKC gene, e.g., by increasing transcription of the PKC gene. In a preferred embodiment, transcription of the PKC gene is increased by: altering the regulatory sequence of the endogenous PKC gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the PKC gene to be transcribed more efficiently.

In another preferred embodiment, Erk kinase is inhibited. An agent which inhibits Erk kinase activity can be one or more of: a specific small molecule which inhibits Erk activity; a Erk binding protein which binds to Erk but does not activate the enzyme; an antibody that specifically binds to the Erk protein, e.g., an antibody that disrupts Erk's catalytic activity; a mutated inactive Erk or fragment which binds to a Erk receptor but does not activate the receptor; a Erk nucleic acid molecule which can bind to a cellular Erk nucleic acid sequence, e.g., mRNA, and inhibit expression of the protein, e.g., an antisense molecule or Erk ribozyme; an agent which decreases Erk gene expression, e.g., a small molecule which binds the promoter of Erk. In another preferred embodiment, Erk is inhibited by decreasing the level of expression of an endogenous Erk gene, e.g., by decreasing transcription of the Erk gene. In a preferred embodiment, transcription of the Erk gene can be decreased by: altering the regulatory sequences of the endogenous Erk gene, e.g., by the addition of a negative regulatory sequence (such as a DNA-biding site for a transcriptional repressor), or by the removal of a positive regulatory sequence (such as an enhancer or a DNA-binding site for a transcriptional activator).

Another aspect of the invention features methods of reducing angiogenesis by decreasing CTGF activity or expression. CTGF activity or expression is decreased by decreasing a VEGF signaling activity by any of the methods described herein. In preferred embodiments, angiogenesis id reduced to, e.g., treat a disorder related to excessive angiogenesis, e.g., tumor growth, tumor metastasis, arthritis, retinal neovascular disease, and retinal ischemia. The method includes administering an agent which decreases CTGF transcription or activity by inhibiting a component of the VEGF signaling pathway, e.g., by any of the agents mentioned above.

Another aspect of the invention features methods of increasing fibrosis.

In a preferred embodiment, the invention features a method of treating disorders related to insufficient fibrosis. The disorder can be the result of an injury. The disorder can be due to a genetic deficiency, a second physiological disorder or disease, or an environmental insult. In a preferred embodiment, the disorder is a wound. In another preferred embodiment the disorder is a damaged organ, e.g., an organ undergoing regeneration. The method includes administering an agent which increases the level of CTGF transcription.

An agent which increases the level of CTGF transcription can be one or more of: an agent which increases the level or activity of VEGF, e.g., a transition metal ion, e.g., manganese, cobalt, nickel, or combinations thereof; an agent which activates the VEGF receptor; an agent which increases PI3 Kinase activity; an agent which increases AKT kinase activity.

In a preferred embodiment, VEGF is increased. An agent which increases the level of VEGF activity can be one or more of the following; a small molecule, e.g., a transition metal ion; a peptide or protein, e.g., a monoclonal antibody, which stabilizes or assists the binding of VEGF to a VEGF receptor; a VEGF polypeptide or a functional fragment or analog thereof; a nucleotide sequence encoding a VEGF polypeptide or functional fragment or analog thereof; an agent which increase VEGF nucleic acid expression; e.g., a small molecule which binds to the promoter region of VEGF. In a preferred embodiment, VEGF levels are increased by administering, e.g., introducing, a nucleotide sequence encoding a VEGF polypeptide or functional fragment or analog thereof, into a particular cell, e.g., an endothelial cell, a fibroblast, or a pericyte, in the subject. The nucleotide sequence can be a genome sequence or a cDNA sequence. The nucleotide sequence can include: a VEGF coding region; a promoter sequence, e.g., a promoter sequence from a VEGF gene or from another gene; an enhancer sequence; untranslated regulatory sequences, e.g., a 5' untranslated region (UTR), e.g., a 5'UTR from a VEGF gene or from another gene, a 3' UTR, e.g., a 3'UTR from a VEGF gene or from another gene; a polyadenylation site; an insulator sequence. In another preferred embodiment, the level of VEGF protein is increased by increasing the level of expression of an endogenous VEGF gene, e.g., by increasing transcription of the VEGF gene. In a preferred embodiment, transcription of the VEGF gene is increased by: altering the regulatory sequence of the endogenous VEGF gene, e.g., by the addition of a positive regulatory element (such as an enhancer or a DNA-binding site for a transcriptional activator); the deletion of a negative regulatory element (such as a DNA-binding site for a transcriptional repressor)and/or replacement of the endogenous regulatory sequence, or elements therein, with that of another gene, thereby allowing the coding region of the VEGF gene to be transcribed more efficiently.

In a preferred embodiment, the VEGF receptor activity is increased. An agent which increases the level of VEGF receptor activity can be one or more of the following: an agent which activates a VEGF receptor, e.g., a monoclonal antibody which activates the VEGF receptor, e.g., a monoclonal antibody which activates a VEGF receptor in the absence of VEGF; a VEGF receptor ligand polypeptide (e.g., VEGF or placenta growth factor (P1GF)), or a functional fragment or analog thereof; a nucleotide sequence encoding a VEGF receptor polypeptide or functional fragment or analog thereof; an agent which increase VEGF receptor nucleic acid expression; e.g., a small molecule which binds to the promoter region of VEGF receptor. In a preferred embodiment, VEGF receptor levels are increased by administering, e.g., introducing, a nucleotide sequence encoding a VEGF receptor polypeptide or functional fragment or analog thereof, into a particular cell, e.g., an endothelial cell, a fibroblast, or a pericyte in the subject. The nucleotide sequence can be a genome sequence or a cDNA sequence. The nucleotide sequence can include: a VEGF receptor coding region; a promoter sequence, e.g., a promoter sequence from a VEGF receptor gene or from another gene; an enhancer sequence; untranslated regulatory sequences, e.g., a 5' untranslated region (UTR), e.g., a 5'UTR from a VEGF receptor gene or from another gene, a 3'UTR, e.g., a 3'UTR from a VEGF receptor gene or from another gene; a polyadenylation site; an insulator sequence. In another preferred embodiment, the level of VEGF receptor protein is increased by increasing the level of expression of an endogenous VEGF receptor gene, e.g., by increasing transcription of the VEGF receptor gene. In a preferred embodiment, transcription of the VEGF receptor gene is increased by: altering the regulatory sequence of the endogenous VEGF receptor gene, e.g., by the addition of a positive regulatory element (such as an enhancer or a DNA-binding site for a transcriptional activator); the deletion of a negative regulatory element (such as a DNA binding site for a transcriptional repressor) and/or replacement of the endogenous regulatory sequence, or elements therein, with that of another gene, thereby allowing the coding region of the VEGF receptor gene to be transcribed more efficiently.

In a preferred embodiment, PI3-Kinase is increased. An agent which increases the level of PI3-kinase can be one or more of the following: a small molecule which activates PI3kinase; a PI3kinase polypeptide or a functional fragment or analog thereof; a nucleotide sequence encoding a PI3kinase polypeptide or functional fragment or analog thereof; an agent which increase PI3-kinase nucleic acid expression, e.g., a small molecule which binds to the promoter region of PI3 kinase. In a preferred embodiment, PI3-kinase levels are increased by administering, e.g., introducing, a nucleotide sequence encoding a PI3-kinase polypeptide or functional fragment or analog thereof, into a particular cell, e.g., an endothelial cell, a fibroblast, or a pericyte, in the subject. The nucleotide sequence can be a genome sequence or a cDNA sequence. The nucleotide sequence can include: a PI3-kinase coding region; a promoter sequence, e.g., a promoter sequence from a PI3 kinase gene or from another gene; an enhancer sequence; untranslated regulatory sequences, e.g., a 5'untranslated region (UTR), e.g., a 5'UTR from a PI3kinase gene or from another gene, a 3'UTR, e.g., a 3'UTR from a PI3-kinase gene or from another gene; a polyadenylation site; an insulator sequence. In another preferred embodiment, the level of PI3kinase protein is increased by increasing the level of expression of an endogenous PI3-kinase gene, e.g., by increasing transcription of the PI3-kinase gene. In a preferred embodiment, transcription of the PI3-kinase gene is increased by: altering the regulatory sequence of the endogenous PI3 kinase gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the PI3-kinase gene to be transcribed more efficiently.

In a preferred embodiment, AKT is increased. An agent which increases the level of AKT can be one or more of the following: a small molecule which activates AKT kinase activity, e.g., the phosphoinositide $PIP_2$; a polypeptide, e.g., insulin, which stimulates activation, e.g., phosphorylation, of AKT; a AKT polypeptide or a functional fragment or analog thereof; a nucleotide sequence encoding a AKT polypeptide or functional fragment or analog thereof; an agent which increase AKT nucleic acid expression; e.g., a small molecule which binds to the promoter region of AKT. In a preferred embodiment, AKT levels are increased by administering, e.g., introducing, a nucleotide sequence encoding a AKT polypeptide or functional fragment or analog thereof, into a particular cell, e.g., an endothelial cell, a fibroblast, or a pericyte, in the subject. The nucleotide sequence can be a genome sequence or a cDNA sequence. The nucleotide sequence can include: a AKT coding region; a promoter sequence, e.g., a promoter sequence from a AKT gene or from another gene; an enhancer sequence; untranslated regulatory sequences, e.g., a 5'untranslated region (UTR), e.g., a 5'UTR from a AKT gene or from another gene, a 3'UTR, e.g., a 3'UTR from a AKT gene or from another gene; a polyadenylation site; an insulator sequence. In another preferred embodiment, the level of AKT protein is increased by increasing the level of expression of an endogenous AKT gene, e.g., by increasing transcription of the AKT gene. In a preferred embodiment, transcription of the AKT gene is increased by: altering the regulatory sequence of the endogenous AKT gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the AKT gene to be transcribed more efficiently.

In another preferred embodiment, Erk kinase is increased. An agent which increases Erk kinase activity can be one or more of: a small molecule which activates Erk kinase activity; an Erk polypeptide or a functional fragment or analog thereof; a nucleotide sequence encoding an Erk polypeptide or functional fragment or analog thereof; an agent which increases Erk nucleic acid expression; e.g., a small molecule which binds to the promoter region of Erk. In a preferred embodiment, Erk levels are increased by administering, e.g., introducing, a nucleotide sequence encoding an Erk polypeptide or functional fragment or analog thereof, into a particular cell, e.g., an endothelial cell, a fibroblast, or a pericyte, in the subject. The nucleotide sequence can be a genome sequence or a cDNA sequence. The nucleotide sequence can include: an Erk coding region; a promoter sequence, e.g., a promoter sequence from an Erk gene or from another gene; an enhancer sequence; untranslated regulatory sequences, e.g., a 5'untranslated region (UTR), e.g., a 5'UTR from an Erk gene or from another gene, a 3'UTR, e.g., a 3'UTR from an Erk gene or from another gene; a polyadenylation site; an insulator sequence. In another preferred embodiment, the level of Erk protein is increased by increasing the level of expression of an endogenous Erk gene, e.g., by increasing transcription of the Erk gene. In a preferred embodiment, transcription of the Erk gene is increased by: altering the regulatory sequence of the endogenous Erk gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Erk gene to be transcribed more efficiently.

Another aspect of the invention features a method of screening for agents which increase or decrease fibrosis and/or angiogenesis to thereby treat disorders associated with increased or decreased fibrosis, e.g., the disorders mentioned above. The method includes: providing a cell, tissue, or subject, e.g., an experimental animal, e.g., an animal model for a fibrosis related disorder; contacting the cell, tissue or subject with a test agent; and determining whether the test agent inhibits a component of the VEGF signaling pathway.

In preferred embodiments, the screening can include screening for: an agent that inhibits VEGF activity; an agent that inhibits VEGFR signaling, e.g., an agent that inhibits the interaction between VEGF and a VEGFR; an agent that inhibits PI3 kinase activity; an agent that inhibits a VEGFR interaction with p85 subunit of PI3-kinase; an agent that inhibits AKT activity; and/or an agent that inhibits ERK activity.

In some embodiments, the method can include one or more of the following steps: applying VEGF to cells in culture, e.g., BREC or BREP; applying a candidate drug or a combinatorial library of drugs; assaying for levels of CTGF. CTGF levels can be assayed various methods commonly practiced in the art. In one embodiment, CTGF levels are assayed by Northern analysis for CTGF mRNA expression. In another embodiment CTGF levels are assayed by detect CTGF protein, e.g., with an antibody, e.g., using an ELISA assay or a Western blot assay. In another embodiment, CTGF transcription is monitored by assaying for a reporter protein, e.g., lacZ, chloramphenicol acetyltransferase (CAT), green fluorescent protein or variants thereof, and other fluorescent proteins and variants thereof, where the gene encoding the reporter protein is fused to the CTGF promoter and the ensemble is transfected into the cells. The methods can further include administering an agent identified by the screening methods described herein to an animal, e.g., an animal model for a fibrotic disorder.

DETAILED DESCRIPTION

The inventors have discovered that VEGF can modulate the activity and/or expression of CTGF in a time- and concentration-dependent manner in cells and/or tissues with VEGF receptors, e.g., in endothelial cells, e.g., microvascular endothelial cells such as human retinal endothelial cells or bovine retinal endothelial cells (BREC), and in contractile cells, e.g., in capillary pericytes, e.g., in human or bovine retinal pericytes (BRPC). VEGF-induced modulation of CTGF can occur via the PI3 kinase pathway, e.g., via the KDR receptor-PI3 kinase-Erk pathway (e.g., in BREC), or the Flt1-PI3 kinase-Akt pathway (e.g., in BRPC). Modulation of CTGF via the VEGF pathway can be used to modulate fibrosis and/or angiogenesis, e.g., in the treatment of fibrosis-related disorders described herein.

VEGF receptor (VEGFR), e.g., Flt1 (VEGFR1), KDR/Flk1 (VEGFR2), Flt4 (VEGFR3), NP1, tie, or tie-2, can mediate increases in CTGF mRNA expression. The ability of Flt1 to induce increases in CTGF mRNA levels is demonstrated in the pericytes that have predominantly Flt1 receptors. In addition, placenta growth factor (P1GF), a Flt1 receptor-specific ligand, was able to induce CTGF mRNA levels in BRPC but not in BREC, indicating that VEGF can induce CTGF mRNA by activating through Flt1 in pericytes, e.g., BRPC. The KDR/Flk1 receptors in the endothelial cells can also induce CTGF gene expression since KDR/Flk1 receptors are the predominant VEGF receptors in endothelial cells.

The VEGF dose-response curves for CTGF in both BRPC and BREC are similar and suggest that VEGF binds to high affinity receptors, consistent with the known Kd values of Flt1 and KDR/Flk1 at 10–100 pM. While not wanting to be bound by theory, VEGF-induced CTGF mRNA is most likely due to an induction of transcription rather than altering the half-life of CTGF mRNA since the addition of VEGF failed to change the degradation rates of CTGF mRNA. The time course of the action of VEGF on CTGF (which required 6–9 h) suggests this is potentially a chronic action of VEGF. In addition, the time needed to achieve maximum effect is also consistent with the calculated mRNA half-life of CTGF mRNA of 2–4 h. From a biological perspective, the effects of VEGF on CTGF mRNA could potentially have important physiological impact for several reasons. First, the increase in CTGF mRNA results in increased protein levels. Second, the VEGF concentration that was minimally active (0.25 ng/ml) can easily bind and activate a significant percentage of the VEGFR-1, -2 receptors. Third, this low level of VEGF may exist even in non-pathological states, suggesting that low levels of VEGF may have physiological actions on maintaining extracellular matrix production via the induction of CTGF. At 2.5–25 ng/ml VEGF which are encountered in hypoxic and angiogenic states (Aiello et al. (1994) N. Engl. J. Med. 331, 1480–1487), the induction of CTGF expression by VEGF could potentially induce the fibrosis that frequently accompanies neovascularization. This possibility is supported further by the demonstration that the protein levels of CTGF expression were increased 10 h after the addition of VEGF that was consistent with the maximum increase in the mRNA levels at 6–9 h. In addition, the potency of VEGF on CTGF expression appeared to be similar to TGF-betal, suggesting that both of them could induce fibrosis associated with neovascularization.

The activation of the endogenous tyrosine kinases of KDR/Flk1s can stimulate multiple signaling pathways, including Ras-Erk, PI3-kinase-Akt, and phospholipase CK-PKC cascades. The results in BREC described herein indicate that VEGF can increase the tyrosine phosphorylation of KDR/Flk1 and its interaction with p85 subunit of PI3-kinase. In addition, VEGF also activates the Erk1/2 pathway in BREC. In contrast, VEGF was unable to activate Erk1/2 but stimulated the activation of PI3-kinase and phosphorylation of Akt in BRPC. These results indicate that the signaling pathways for Flt1 in vascular cells are different from those for KDR/Flk1. The lack of effect on Erk1/2 activation also supports the hypothesis that Flt1, unlike KDR/Flk1, is not involved in mitogenic actions.

The results described herein provide strong evidence that VEGF is inducing CTGF gene expression in both endothelial cells and pericytes via VEGFR1 or -R2 by the activation of PI3-kinase and Akt. This evidence includes the ability of wortmannin, a PI3-kinase inhibitor, to inhibit the effects of VEGFs in both cell types. Adenovirus containing dominant negative mutants of p85 subunit of PI3-kinase or Akt inhibited the action of VEGFs, whereas overexpression of dominant negative mutants of Ras and Erk1 by adenovirus vectors did not inhibit CTGF mRNA expression. Conversely, the overexpression of constitutive active Akt increased CTGF mRNA expression by 2.5-fold. The overexpression of either the wild type or dominant negative of PKC isoform did not alter the effects of VEGF on CTGF mRNA levels.

In summary, the results described herein show that VEGF can induce the expression of CTGF via VEGFR, e.g., Flt1, KDR/Flk1, Flt4, NP-1, tie, or tie-2, by the selectively activated PI3-kinase-Akt pathway but mostly independent of the Ras-Erk pathway. In addition, the spectrum of signaling pathways can be different among different VEGFRs, possibly reflecting their physiological roles. These results support the conclusion that VEGF, through its effects on CTGF expression, has physiological roles such as the maintenance of capillary strength and wound healing via the extracellular matrix production. In disease states, VEGF-induced CTGF may cause the proliferation of fibrocellular components in retinal neovascular diseases such as proliferative diabetic retinopathy and age-related macular degeneration.

Modulation of CTGF through the VEGF pathway, e.g., modulation of components of the VEGF pathway, e.g., Flt1, KDR, Flt4, neuropilin-1, PI3 kinase, Akt, or Erk, can be used to modulate fibrosis and/or angiogenesis, e.g., in the treatment of fibrosis related disorders. CTGF has been associated with a number of fibrosis-related disorders, e.g., scleroderma (e.g., morphea, generalized morphea, linear scleroderma); keloids; kidney fibrosis, e.g., glomerular sclerosis or renal tubulointerstitial fibrosis; pulmonary fibrosis; cardiac fibrosis; chemotherapy/radiation induced lung fibrosis; pancreatitis; renal disease; atherosclerotic plaques; inflammatory bowel disease; Crohn's disease; arthritic joints; cancer, e.g., invasive breast carcinoma, dermatofibromas, angiolipoma, and angioleiomyoma; hypertrophic scar; nodular fasciitis, eosinophilic fasciitis, dupuytren's contracture (J. Invest. Dermatol. 1996 106:729–733; J Biol Chem. 2001 276: 10594–601; Int J Biochem Cell Biol. 1998 30:909–22; J Eur Acad Dermatol Venereol. 1998 11:1–8; Int J Biochem Cell Biol. 1998 August;30(8):909–22; Ann Surg. 1999 July; 230(1):63–71; J Cell Physiol. 1999 October;181(1):153–9; Curr Opin Nephrol Hypertens. 1999 September;8(5):543–8; J Am Soc Nephrol. 2001 March;12(3):472–84; J Rheumatol. 2000 January;27(1):149–54; J Mol Cell Cardiol. 2000 October;32(10): 1805–19). Other fibrosis related diseases in which CTGF may be involved include macular degeneration, e.g., age-related macular degeneration; acute ocular neovascularization or diabetic retinopathy; general fibrosis syndrome, characterized by replacement of normal muscle tissue by fibrous tissue in varying degrees; retroperitoneal fibrosis; liver fibrosis; acute fibrosis, e.g., in response to various forms of trauma including accidental injuries, infections, surgery, burns, radiation or chemotherapy treatments.

Generation of Fragments

Fragments of components of the VEGF signaling pathway, e.g., VEGF, VEGFRs, PI3 kinase, AKT, can be used to increase VEGF signaling, thereby increasing CTGF activity, thereby increasing fibrosis or angiogenesis. For example, various fragments of VEGF are known and described, for example, in U.S. Pat. No. 5,935,820.

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein, e.g., a VEGF signaling pathway component described herein, can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants, e.g., screening for CTGF modulating activity or VEGF signaling agonist or antagonist activity, are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* (1978) USA, 75: 5765).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with a component of the VEGF signaling pathway, e.g., VEGF, VEGFR (e.g., flt1, flt4, KDR, neuropilin), PI3 kinase (e.g., p85), AKT, ERK. These may include agonists, superagonists, and antagonists of the components. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., a VEGF or VEGFR molecule or a fragment thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267: 16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ.* *Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the *Staphylococcus* protein A and the outer membrane protease IgA of *Neisseria* (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest (e.g., VEGF or PI3kinase) and a ligand (e.g., VEGFR and AKT, respectively) can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject polypeptides, e.g., VEGF or VEGFR, to generate mimetics, e.g. peptide or non-peptide agents. See, for example, "Peptide inhibitors of human papillomavirus protein binding to retinoblastoma gene protein" European patent applications EP 0 412 762 and EP 0 031 080.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Fusion Proteins

Polypeptides for modulating the level of a component of the VEGF signaling pathway can be fused to another protein or portion thereof. For example, a VEGF protein or antagonist or fragment thereof, can be operably linked to another polypeptide moiety to enhance solubility. Examples of a protein which can be fused with a protein or portions thereof include a plasma protein or fragment thereof, which can improve the circulating half life. For example, the fusion protein can be a VEGF fragment-immunoglobulin (Ig) fusion protein in which the VEGF sequence is fused to a sequence derived from the immunoglobulin superfamily. Several soluble fusion protein constructs have been disclosed wherein the extracellular domain of a cell surface glycoprotein is fused with the constant F(c) region of an immunoglobulin. For example, Capon et al. (1989) *Nature* 337(9):525–531, provide guidance on generating a longer lasting CD4 analog by fusing CD4 to an immunoglobulin (IgG1). See also, Capon et al., U.S. Pat. Nos. 5,116,964 and 5,428,130 (CD4-IgG fusion constructs); Linsley et al., U.S. Pat. No. 5,434,131 (CTLA4-IgG1 and B7-IgG1 fusion constructs); Linsley et al. (1991) *J. Exp. Med.* 174:561–569 (CTLA4-IgG1 fusion constructs); and Linsley et al. (1991) *J. Exp. Med.* 173:721–730 (CD28-IgG1 and B7-IgG1 fusion constructs). Such fusion proteins have proven useful for modulating receptor-ligand interactions and reducing inflammation in vivo. For example, fusion proteins in which an extracellular domain of cell surface tumor necrosis factor receptor (TNFR) proteins has been fused to an immunoglobulin constant (Fc) region have been used in vivo. See, for example, Moreland et al. (1997) *N. Engl. J Med.* 337(3): 141–147; and, van der Poll et al. (1997) *Blood* 89(10): 3727–3734).

Antibodies

The invention also includes antibodies specifically reactive with a component of the VEGF signaling pathway described herein. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

A component of the VEGF signaling pathway described herein, or a portion or fragment thereof, can be used as an immunogen to generate antibodies that bind the component using standard techniques for polyclonal and monoclonal antibody preparation. The full-length component protein can be used or, alternatively, antigenic peptide fragments of the component can be used as immunogens.

Typically, a peptide is used to prepare antibodies by immunizing a suitable subject, (e.g., rabbit, goat, mouse or other mammal) with the immunogen. An appropriate immunogenic preparation can contain, for example, a recombinant VEGF peptide, or a chemically synthesized VEGF peptide or anagonist. See, e.g., U.S. Pat. No. 5,460,959 which is hereby expressly incorporated by reference in its entirety. The nucleotide and amino acid sequences of components of the VEGF signaling pathway described herein are known. The preparation can further include an adjuvant, such as Freund's complete or incomplete adjuvant, or similar immunostimulatory agent. Immunization of a suitable subject with an immunogenic VEGF preparation induces a polyclonal anti-VEGF antibody response.

Antibodies to a component of the VEGF signaling pathway, or fragments thereof, can be used to inhibit the levels of such a component, thereby decreasing CTGF activity. Examples of antibody fragments include F(v), Fab, Fab' and F(ab')$_2$ fragments which can be generated by treating the antibody with an enzyme such as pepsin. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

Additionally, antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Application No. PCT/US86/02269 (now WO 87/02671); Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., *Science* 240:1041–1043, 1988; Liu et al., *PNAS* 84:3439–3443, 1987; Liu et al., *J. Immunol.* 139:3521–3526, 1987; Sun et al. *PNAS* 84:214–218, 1987; Nishimura et al., *Canc. Res.* 47:999–1005, 1987; Wood et al., *Nature* 314:446–449, 1985; and Shaw et al., *J. Natl. Cancer Inst.* 80:1553–1559, 1988); Morrison, S. L., *Science* 229:1202–1207, 1985; Oi et al., *BioTechniques* 4:214, 1986; Winter U.S. Pat. No. 5,225,539; Jones et al., *Nature* 321: 552–525, 1986; Verhoeyan et al., *Science* 239:1534, 1988; and Beidler et al., *J. Immunol.* 141:4053–4060, 1988.

In addition, a human monoclonal antibody directed against a component of the VEGF signaling pathway described herein can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. Pct publication WO 94/04667; Ditullio et al. PCT publication WO 95/17085; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci. USA* 81:6851–6855; Bruggeman et al. (1993) *Year Immunol* 7:33–40; Choi et al. (1993) *Nature Genet.* 4:117–123; Tuaillon et al. (1993) *PNAS* 90:3720–3724; Bruggeman et al. (1991) *Eur J Immunol* 21:1323–1326); Duchosal et al. PCT publication WO 93/05796; U.S. Pat. No. 5,411,749; McCune et al. (1988) *Science* 241:1632–1639), Kamel-Reid et al. (1988) *Science* 242:1706; Spanopoulou (1994) *Genes & Development* 8:1030–1042; Shinkai et al. (1992) *Cell* 68:855–868). A human antibody-transgenic mouse or an immune deficient mouse engrafted with human antibody-producing cells or tissue can be immunized with a component of the VEGF signaling pathway described herein or an antigenic peptide thereof and splenocytes from these immunized mice can then be used to create hybridomas. Methods of hybridoma production are well known.

Human monoclonal antibodies against components of the VEGF signaling pathway described herein can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) *J. Mol. Biol.* 222:581–597; and Griffths et al. (1993) *EMBO J* 12:725–734. In addition, a combinatorial library of antibody variable regions can be generated by mutating a known human antibody. For example, a variable region of a human antibody known to bind VEGF, can be mutated, by for example using randomly altered mutagenized oligonucleotides, to generate a library of mutated variable regions which can then be screened to bind to VEGF. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) *Proc. Nat'l Acad. Sci. USA* 89:4457–4461.

The immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) supra; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al.

(1991) *Nuc Acid Res* 19:4133–4137; and Barbas et al. (1991) *PNAS* 88:7978–7982. Once displayed on the surface of a display package (e.g., filamentous phage), the antibody library is screened to identify and isolate packages that express an antibody that binds a component of the VEGF signaling pathway described herein. In a preferred embodiment, the primary screening of the library involves panning with an immobilized component of the VEGF signaling pathway described herein and display packages expressing antibodies that bind immobilized a component of the VEGF signaling pathway described herein are selected.

Antisense Nucleic Acid Sequences

Nucleic acid molecules which are antisense to a nucleotide encoding a component of the VEGF signaling pathway described herein, e.g., VEGF, VEGFR (e.g., flt1, flt4, KDR, neuropilin), PI3Kinase, AKT, can be used as an agent which inhibits expression of the component. An "antisense" nucleic acid includes a nucleotide sequence which is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule which antisense to the "coding region" of the coding strand of a nucleotide sequence encoding the component can be used.

The coding strand sequences encoding components of the VEGF signaling pathway described herein are known. Given the coding strand sequences encoding these components, antisense nucleic acids can be designed according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Administration

An agent which modulates the level of expression of a component of the VEGF signaling pathway described herein can be administered to a subject by standard methods. For example, the agent can be administered by any of a number of different routes including intravenous, intradermal, subcutaneous, oral (e.g., inhalation), transdermal (topical), and transmucosal. In one embodiment, the VEGF signaling pathway modulating agent can be administered topically.

The agent which modulates protein levels, e.g., nucleic acid molecules, polypeptides, fragments or analogs, modulators, and antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (non-ionic solubilizer and emulsifier; BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a VEGF polypeptide or anti-VEGF antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., *PNAS* 91:3054–3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

The agent which modulates the activity of a component of the VEGF signaling pathway described herein can be administered by locally administration, e.g., topical administration. The agent can be applied once or it can be administered continuously, e.g., the agent is administered with sufficient frequency such that the affect on the VEGF protein level is maintained for a selected period, e.g., 5, 10, 20, 30, 50, 90, 180, 365 days or more. The administration of an agent which modulates, e.g., increases or inhibits, the level of a component of the VEGF signaling pathway described herein, e.g., a VEGF polypeptide or an anti-VEGF antibody, can also be repeated.

Transition Metals

Transition metal ions have been shown to enhance expression of the VEGF gene thereby increasing VEGF protein levels. See U.S. Pat. No. 5,480,975. Thus, in one aspect, a transition metal ion can be used to increase CTGF, thereby increasing fibrosis or angiogenesis, by increasing expression of VEGF.

The transition metals are the group consisting of the fourth, fifth and sixth levels of the periodic table and which fill the d orbital. They include such elements as Ni, Co, Mn, Zn, V, Cr, Fe, Cu, Mo, etc. The preferred candidate metal ions for use are manganese, cobalt and nickel.

Selection of other appropriate metal ions involves determining whether, and at what level, the ion will induce VEGF expression. Particularly for systemic applications, selection also involves a review of toxicity. Suitable techniques for those determinations are provided below in U.S. Pat. No. 5,480,795. Preferred ions are those with a substantial range between VEGF induction and toxicity.

The transition metal can be administered internally (systemic or local administration) in the form of a salt or free ion in a biologically compatible tablet or capsule, gel, or liquid, or it can be administered externally in the form of a biologically compatible powder, salve, liquid, or transdermal patch. Any physiologically acceptable anion such as chloride, sulfate, etc., can be included in the composition.

Appropriate release rates and dosages can be determined in order to affect the targeted tissue without substantial systemic effect. For example, these parameters can be determined as described in U.S. Pat. No. 5,480,795.

Gene Therapy

The gene constructs of the invention can also be used as a part of a gene therapy protocol to deliver nucleic acids encoding either an agonistic or antagonistic form of a component of the VEGF signaling pathway described herein. The invention features expression vectors for in vivo transfection and expression of a component of the VEGF signaling pathway described herein in particular cell types so as to reconstitute the function of, or alternatively, antagonize the function of the component in a cell in which that polypeptide is misexpressed. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a component of the VEGF signaling pathway described herein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Immunol. 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

In addition to viral transfer methods, such as those illustrated above, non-viral methods can also be employed to cause expression of a component of the VEGF signaling pathway described herein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al. (2001) J Invest Dermatol. 116(1): 131–135; Cohen et al. (2000) Gene Ther 7(22):1896–905; or Tam et al. (2000) Gene Ther 7(21):1867–74.

In a representative embodiment, a gene encoding a component of the VEGF signaling pathway described herein can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Cell Therapy

A component of the VEGF signaling pathway described herein can also be increased in a subject by introducing into a cell, e.g., an endothelial call, fibroblast or a keratinocyte, a nucleotide sequence that modulates the production of the component, e.g., a nucleotide sequence encoding a component polypeptide or functional fragment or analog thereof, a promoter sequence, e.g., a promoter sequence from a VEGF gene or from another gene; an enhancer sequence, e.g., 5' untranslated region (UTR), e.g., a 5' UTR from a VEGF gene or from another gene, a 3' UTR, e.g., a 3' UTR from a VEGF gene or from another gene; a polyadenylation site; an insulator sequence; or another sequence that modulates the expression of VEGF. The cell can then be introduced into the subject.

Primary and secondary cells to be genetically engineered can be obtained form a variety of tissues and include cell types which can be maintained propagated in culture. For example, primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding a component of the VEGF signaling pathway described herein or an agonist or antagonist thereof, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electrophoration, all of which are routine in the art.

Transfected primary or secondary cells undergo sufficient number doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from fibrosis is a candidate for implantation of cells producing an antagonist of a component of the VEGF signaling pathway described herein.

An immunosuppressive agent e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) N. Engl. J. Med. 327:1549; Spencer et al. (1992) N. Engl. J. Med. 327:1541+ Widner et al. (1992) n. Engl. J. Med. 327:1556). Dosage values may vary according to factors such as the disease state, age, sex, and weight of the individual.

EXAMPLES

Example 1

VEGF Modulates CTGF mRNA Expression

The effects of VEGF on the expression of CTGF mRNA were studied by Northern blot analysis in BREC and BRPC. 25 ng/ml VEGF increased CTGF mRNA (~2.4 kb) levels in a time-dependent manner, reaching a maximum after 6 h in BREC ($3.1\pm0.70$-fold, $p<0.001$) and after 9 h in BRPC ($2.0\pm0.22$-fold, $p<0.01$).

The dose response to VEGF-induced CTGF mRNA expression was studied after 6 h of VEGF stimulation. The expression of CTGF mRNA was up-regulated in a dose-dependent manner, with significant increases observed at concentrations as low as 0.25 ng/ml in both BREC and BRPC. Maximal increases were observed at VEGF concentrations of 25 ng/ml in both BREC and BRPC.

Since BREC and BRPC may express both KDR and Flt1, we examined the effects of P1GF, a Flt1-specific ligand, on the induction of CTGF gene expression in vascular cells. CTGF mRNA levels were not affected after stimulation of 25 ng/ml of P1GF in BREC. In contrast, P1GF increased CTGF mRNA after 3 h of stimulation, which peaked after 9 h in BRPC ($1.9\pm0.30$-fold, $p<0.01$), suggesting that VEGF-induced CTGF gene expression was mediated primarily by KDR in BREC and Flt1 in BRPC.

Example 2

VEGF Induction of CTGF Protein Production

To determine if the effects of VEGF on CTGF mRNA were correlated with its protein level, CTGF protein expression was assessed by Western blot analysis using anti-human CTGF antibody. The detected size of CTGF protein was ~38 kDa in both BREC and BRPC. VEGF (25 ng/ml) increased the level of CTGF protein after 10 h in both BREC and BRPC. Comparative studies were performed on the effects of VEGF (25 ng/ml) and TGF-$\beta$1 (10 ng/ml) on the expression of CTGF mRNA and protein. VEGF and TGF-$\beta$1 increased CTGF protein expression by a similar amount ($2.5\pm0.4$- and $2.8\pm0.8$-fold, respectively, in BREC). CTGF mRNA levels were also increased a similar extent ($3.0\pm0.3$- and $3.3\pm0.5$-fold, respectively).

Example 3

Effects of VEGF on the Half-life of CTGF mRNA

The effects of VEGF on the stability of CTGF mRNA were examined. Northern blot analyses were performed with addition of actinomycin D (5 µg/ml) after 6 h of VEGF (25 ng/ml) stimulation. In BREC and BRPC3, the half-life of CTGF mRNA was 1.7 and 3.6 h, respectively. There was no significant difference between VEGF-treated and -untreated cells.

Example 4

Effects of Cycloheximide on CTGF mRNA Regulation

In order to examine the possibility that VEGF regulates CTGF mRNA expression through new protein synthesis of cytokines or transcription factors, cells were treated for 6 h with VEGF (25 ng/ml) and a protein synthesis inhibitor, cycloheximide (10 µg/ml). Cycloheximide did not prevent the increase of CTGF mRNA. Addition of both VEGF and cycloheximide increased CTGF mRNA $2.4\pm0.41$-fold in BREC and $2.5\pm0.40$-fold in BRPC after 6 h as compared with cycloheximide alone ($p<0.01$). These data suggest that the stimulation of CTGF mRNA expression by VEGF was not induced by increased synthesis of a regulatory protein.

Example 5

Involvement of Erk and PI3-Kinase-Akt in VEGF Signaling

Since Erk and PI3-kinase-Akt pathways have been reported to play central roles in VEGF signaling and biological actions, it was investigated whether or not VEGF can activate Erk and PI3-kinase-Akt pathways equally in BREC and BRPC. Immunoblot analysis of immunoprecipitates of KDR from BREC stimulated with VEGF or P1GF using an antibody to phosphotyrosine and PI3-kinase p85 subunit demonstrated that VEGF, but not P1GF, promoted the tyrosine phosphorylation of KDR and interactions of KDR and p85 subunit of PI3-kinase. In contrast, Immunoblot analysis of immunoprecipitates of Flt1 from BRPC stimulated with VEGF or P1GF demonstrated that both VEGF and P1GF increased the tyrosine phosphorylation of Flt1 and interactions of Flt1 and p85 subunit of PI3-kinase. These data suggest that VEGF can activate the receptor tyrosine phosphorylation and interaction with PI3-kinase p85 subunit in both KDR and Flt1.

To investigate the activation of Akt and Erk, we next performed immunoblot analysis with anti-phosphorylated Akt or anti-phosphorylated Erk antibodies using total cell lysates from BREC or BRPC stimulated with VEGF. VEGF induced phosphorylation of both Akt and Erk in BREC by 3.1- and 5.8-fold, but only induced phosphorylation of Akt in BRPC by 2.6-fold. No effect on Erk phosphorylation was observed in BRPC. These data suggest that VEGF activated both Erk and PI3-kinase-Akt pathways in BREC, but stimulated only PI3-kinase-Akt pathway in BRPC.

Since the activation of PI3-kinase by VEGF has not been reported in BRPC, we studied the effects of VEGF on PI3-kinase activity in BRPC. The addition of VEGF (25 ng/ml) increased PI3-kinase activity in a time-dependent manner by $2.1\pm0.27$-fold ($p<0.01$) after 5 min and by $1.6\pm0.17$-fold ($p<0.05$) after 10 min in BRPC.

Example 6

Effects of PKC, Erk, and PI3-Kinase Inhibition on VEGF-induced CTGF Expression To investigate the signaling pathways involved in VEGF-induced CTGF expression, the effects of inhibition of PKC, Erk, and PI3-kinase were determined. Cells were treated with 25 ng/ml VEGF for 6 h after pretreatment with the kinase inhibitor GF 109203X, a classical and novel PKC-specific inhibitor (1 µM); PD98059, a MAPK/Erk kinase inhibitor (20 µM); or wortmannin, a PI3-kinase inhibitor (100 nM). Neither GF 109203X nor PD98059 had significant effects on VEGF-induced CTGF mRNA expression, but wortmannin inhibited the effects of VEGF by 88±6.5% ($p<0.01$) in BREC and 78±22% ($p<0.01$) in BRPC. To confirm further the involvement of PI3-kinase in VEGF-induced CTGF expression, recombinant adenoviruses were used encoding dominant negative K-ras (DNRas), dominant negative extracellular signal-regulated kinase (DNErk), or Δp85 of PI3-kinase. BREC were transfected with each adenoviral vector, followed by stimulation with 25 ng/ml VEGF for 6 h. Neither DNRas nor DNErk had significant effects on VEGF-induced increase in CTGF mRNA, but Δp85 of PI3-kinase completely inhibited VEGF-induced CTGF expression ($p<0.001$).

Example 7

Role of PKCζ and Akt/PKB in VEGF-induced CTGF Expression

Since it has been reported that atypical PKC and Akt/PKB have significant roles as signaling molecules downstream of PI3-kinase, the involvement of PKCζ and Akt in this process were examined. BREC were infected with each adenoviral vector, followed by stimulation with 25 ng/ml VEGF for 6 h. Neither wild type PKCζ nor dominant negative PKCζ (DNPKCζ) had significant effects on VEGF-induced increase in CTGF mRNA. In contrast, infection with constitutive active Akt (CAAkt) increased CTGF mRNA expression 2.1±0.21-fold ($p<0.01$) without VEGF and 2.5±0.40-fold with VEGF. Overexpression with adenoviral vector containing dominant negative Akt (DNAkt) inhibited VEGF-induced CTGF expression by 85±13% ($p<0.01$).

Example 8

Methods

A) Materials—Endothelial cell basal medium was purchased from Clonetics (San Diego, Calif.). Endothelial cell growth factor was purchased from Roche Molecular Biochemicals. Dulbecco's modified Eagle's medium and fetal bovine serum were obtained from Life Technologies, Inc. VEGF, placenta growth factor (P1GF), TGF-β1, and anti-CTGF antibody were ordered from R & D Systems (Minneapolis, Minn.). Anti-KDR (Flk1) and anti-Flt1 antibodies were purchased from Santa Cruz Biotechnology (Santa Cruz, Calif.). Protein A-Sepharose was purchased from Amersham Pharmacia Biotech. Anti-phospho-Erk, anti-Erk, anti-phospho-Akt, and anti-Akt were purchased from New England Biolabs (Beverly, Mass.). Anti-p85 and anti-phosphotyrosine were purchased from Upstate Biotechnology, Inc. (Lake Placid, N.Y.). Phosphatidylinositol (PI) was purchased from Avanti (Alabaster, Ala.), and PD98059, wortmannin, and GF 109203X were obtained from Calbiochem. All other materials were ordered from Fisher and Sigma.

B) Cell Culture—Primary cultures of bovine retinal endothelial cells (BREC) and pericytes (BRPC) were isolated by homogenization and a series of filtration steps as described previously. BREC were subsequently cultured with endothelial cell basal medium supplemented with 10% plasma-derived horse serum, 50 mg/liter heparin, and 50 µg/ml endothelial cell growth factor. BRPC were cultured in Dulbecco's modified Eagle's medium with 5.5 mM glucose and 20% fetal bovine serum. Cells were cultured in 5% $CO_2$ at 37° C., and media were changed every 3 days. Cells were characterized for their homogeneity by immunoreactivity with anti-factor VIII antibody for BREC and with monoclonal antibody 3G5 for BRPC. Cells remained morphologically unchanged under these conditions, as confirmed by light microscopy. Only cells from passages 2 through 7 were used for the experiments.

C) Recombinant Adenoviruses—cDNA of constitutive active Akt (CAAkt, Gag protein fused to N-terminal of wild type Akt) was constructed as in Burgering et al. (1995) *Nature* 376, 599–602. cDNA of dominant negative Akt (DNAkt, substituted Thr-308 to Ala and Ser-473 to Ala) was constructed as described in Kitamura et al. (1998) *Mol. Cell. Biol.* 18, 3708–3717. cDNA of dominant negative K-Ras (DNRas, substituted Ser-17 to Asn) was kindly provided by Dr. Takai (Osaka University). cDNA of dominant negative extracellular signal-regulated kinase (DNErk, substituted Lys-52 to Arg in ATP-binding site) was constructed as described in Her et al. (1993) *Biochem. J.* 296, 25–3. cDNA of Δp85 was kindly provided by Dr. Kasuga (Kobe University). cDNA of PKCζ was kindly provided by Dr. Douglas Ways (Lilly). cDNA of dominant negative PKCζ (DNPKCζ, substituted Lys-273 to Trp in ATP-binding site) was constructed as in Uberall et al. (1999) *J. Cell Biol.* 144, 413–425

The recombinant adenoviruses were constructed by homologous recombination between the parental virus genome and the expression cosmid cassette or shuttle vector. The adenoviruses were applied at a concentration of $1\times10^8$ plaque-forming units/ml, and adenoviruses with the same parental genome carrying the lacZ gene or enhanced green fluorescein protein gene (CLONTECH, Palo Alto, Calif.) were used as controls. Expression of each recombinant protein was confirmed by Western blot analysis and increased about 10-fold compared with cells infected with the control adenovirus.

D) Immunoprecipitation—Cells were washed three times with cold phosphate-buffered saline and solubilized in 200 µl of lysis buffer (1% Triton X-100, 50 mmol/liter HEPES, 10 mmol/liter EDTA, 10 mmol/liter sodium pyrophosphate, 100 mmol/liter sodium fluoride, 1 mmol/liter sodium orthovanadate, 1 µg/ml aprotinin, 1 µg/ml leupeptin, and 2 mmol/liter phenylmethylsulfonyl fluoride). After centrifugation at 12,000 rpm for 10 min, 1.0 mg of protein was subjected to immunoprecipitation. To clear the protein extract, protein A-Sepharose (20 µl of a 50% suspension) was added to the cell lysates, after which they were incubated for 1 h, followed by centrifugation and collection of the supernatant. A specific rabbit anti-KDR or Flt1 antibody was added and rocked at 4° C. for 2 h; 20 µl of protein A-Sepharose was then added, and the sample was rocked for another 2 h at 4° C. For denaturation, protein A-Sepharose antigen-antibody conjugates were separated by centrifugation, washed five times, and boiled for 3 min in Laemmli sample buffer.

E) Western Blot Analysis—Immunoprecipitated proteins or 30 µg of total cell lysates were subjected to SDS-gel electrophoresis and electrotransferred to nitrocellulose membrane (Bio-Rad). The membrane was soaked in blocking buffer (phosphate-buffered saline containing 0.1% Tween 20 and 5% bovine serum albumin) for 1 h at room temperature and incubated with primary antibody overnight at 4° C. followed by incubation with horseradish peroxidase-conjugated secondary antibody (Amersham Pharmacia Biotech). Visualization was performed using the enhanced chemiluminescence detection system (ECL, Amersham Pharmacia Biotech) per the manufacturer's instructions.

F) PI3-Kinase Assay—PI3-kinase activities were measured by the in vitro phosphorylation of PI as in Xia et al. (1996) J. Clin. Invest. 98, 2018–2026. Cells were lysed in ice-cold lysis buffer containing 50 mM HEPES, pH 7.5, 137 mM NaCl, 1 mM $MgCl_2$, 1 mM $CaCl_2$, 2 mM $Na_3VO_4$, 10 mM NaF, 2 mM EDTA, 1% Nonidet P-40, 10% glycerol, 1 mM phenylmethylsulfonyl fluoride, 2 µg/ml aprotinin, 5 µg/ml leupeptin, and 1 µg/ml pepstatin. Insoluble material was removed by centrifugation at 15,000×g for 10 min at 4° C. PI3-kinase was immunoprecipitated from aliquots of the supernatant with antiphosphotyrosine antibodies. After successive washings, the pellets were resuspended in 50 µl of 10 mM Tris, pH 7.5, 100 mM NaCl, and 1 mM EDTA. 10 µl of 100 mM $MgCl_2$ and 10 µl of PI (2 µg/µl) sonicated in 10 mM Tris, pH 7.5, with 1 mM EGTA was added to each pellet. The PI3-kinase reaction was initiated by the addition of 5 µl of 0.5 mM ATP containing 30 µCi of [$\gamma$-$^{32}$P]ATP. After 10 min at room temperature with constant shaking, the reaction was stopped by the addition of 20 µl of 8 N HCl and 160 µl of chloroform/methanol (1:1). The samples were centrifuged, and the organic phase was removed and applied to silica gel TLC plates developing in $CHCl_3/CH_3OH/H_2O/NH_4OH$ (60:47:11:2). The radioactivity in spots was quantified by PhosphorImager (Molecular Dynamics, Sunnyvale, Calif.).

G) Amplification of Human CTGF cDNA Using Reverse Transcriptase-Polymerase Chain Reaction (PCR)—cDNA templates for PCR were synthesized by reverse transcriptase (First Strand cDNA Synthesis Kit, Amersham Pharmacia Biotech) from human fibroblast according to the method recommended by the manufacturer. A standard PCR was performed (PCR optimizer kit, Invitrogen, Carlsbad, Calif.) using 5'-AGGGCCTCTTCTGTGACTTCG-3' (sense primer, SEQ ID NO:1) and 5'-TCATGCCATGTCTCCGTACATC-3' (antisense primer, SEQ ID NO:2). The PCR products were then subcloned into a vector (pCRII, Invitrogen) and sequenced in their entirety, and comparison with the published human sequences revealed complete sequence identity. This cDNA probe was used for hybridization.

H) Northern Blot Analysis—Total RNA was isolated using acid-guanidinium thiocyanate, and Northern blot analysis was performed. Total RNA (20 µg) was electrophoresed through 1% formaldehyde-agarose gels and then transferred to a nylon membrane. $^{32}$P-Labeled cDNA probes were generated by use of labeling kits (Megaprime DNA labeling systems, Amersham Pharmacia Biotech). After ultraviolet cross-linking using a UV cross-linker (Stratagene, La Jolla, Calif.), blots were pre-hybridized, hybridized, and washed in 0.5×SSC, 5% SDS at 65° C. with 4 changes over 1 h. All signals were analyzed using a PhosphorImager, and lane loading differences were normalized.

I) Analysis of CTGF mRNA Half-life—CTGF mRNA half-life experiments were carried out using BREC and BRPC. The cells were exposed to vehicle or VEGF (25 ng/ml) for the indicated periods prior to mRNA stability measurements. Transcription was inhibited by the addition of actinomycin D (5 µg/ml). For inhibition of protein synthesis, cells were treated with cycloheximide (10 µg/ml) for the times indicated.

J) Statistical Analysis—Determinations were performed in triplicate, and all experiments were repeated at least three times. Results are expressed as the mean±S.D., unless otherwise indicated. Statistical analysis employed Student's t test or analysis of variance to compare quantitative data populations with normal distributions and equal variance. Data were analyzed using the Mann-Whitney rank sum test or the Kruskal-Wallis test for populations with non-normal distributions or unequal variance. A p value of <0.05 was considered statistically significant.

All patents and references cited herein are hereby incorporated by reference in their entirety.

I claim:

1. A method of decreasing fibrosis in a tissue of a subject, the method comprising:
   identifying a subject in need of decreased fibrosis, wherein the subject has a disorder selected from the group consisting of scleroderma; keloids; kidney fibrosis; pulmonary fibrosis; cardiac fibrosis; chemotherapy/radiation induced lung fibrosis; pancreatitis; inflammatory bowel disease; Crohn's disease; hypertrophic scar; nodular fasciitis; eosinophilic fasciitis; Dupuytren's contracture; general fibrosis syndrome, characterized by replacement of normal muscle tissue by fibrous tissue in varying degrees; retroperitoneal fibrosis; liver fibrosis; and acute fibrosis; and
   administering to the subject an antibody or antigen-binding fragment thereof that binds to VEGF receptor 1 (VEGFR1) and inhibits a VEGF-VEGFR1 signalling activity, thereby decreasing fibrosis in the tissue of the subject.

2. The method of claim 1, wherein the antibody or antigen-binding fragment thereof decreases the level of available VEGFR1.

3. The method of claim 1, wherein the tissue is skin tissue, lung tissue, cardiac tissue, kidney tissue, liver tissue, or retinal tissue.

4. The method of claim 1, wherein the antibody or antigen binding fragment thereof is an anti-VEGFR1/flt1 inhibitory antibody or antigen binding fragment thereof.

5. The method of claim 4, wherein the antibody is a monoclonal antibody.

6. The method of claim 4, wherein the antigen binding fragment is an F(v), Fab, Fab' or F(ab')$_2$ anti-VEGFR1 antibody fragment.

7. The method of claim 4, wherein the antibody is a chimeric or humanized antibody.

8. A method of decreasing fibrosis in a tissue of a subject, the method comprising:
   identifying a subject in need of decreased fibrosis, wherein the subject has a disorder selected from the group consisting of scleroderma; keloids; kidney fibrosis; pulmonary fibrosis; cardiac fibrosis; chemotherapy/radiation induced lung fibrosis; pancreatitis; inflammatory bowel disease; Crohn's disease; hypertrophic scar; nodular fasciitis; eosinophilic fasciitis; Dupuytren's contracture; general fibrosis syndrome, characterized by replacement of normal muscle tissue by fibrous tissue in varying degrees; retroperitoneal fibrosis; liver fibrosis; and acute fibrosis; and
   administering to the subject an antibody or antigen binding fragment thereof that binds to VEGF and inhibits a VEGF-VEGF Receptor 1 (VEGFR1) signalling activity, thereby decreasing fibrosis in the tissue of the subject.

9. The method of claim 8, wherein the antibody or antigen binding fragment thereof decreases the level of VEGF, thereby inhibiting a VEGF—VEGF Receptor 1 (VEGFR1) signalling activity.

10. The method of claim 8, wherein the subject has a fibrosis-related disorder.

11. The method of claim 8, wherein the tissue is skin tissue, lung tissue, cardiac tissue, kidney tissue, liver tissue, or retinal tissue.

12. The method of claim 8, wherein the antibody is a monoclonal antibody.

13. The method of claim 8, wherein the antigen binding fragment is an F(v), Fab, Fab' or F(ab')$_2$ anti-VEGF antibody fragment.

14. The method of claim 8, wherein the antibody is a chimeric or humanized antibody.

15. The method of claim 8, wherein the scleroderma is morphea, generalized morphea, or linear scleroderma.

16. The method of claim 8, wherein the kidney fibrosis is glomerular sclerosis or renal tubulointerstitial fibrosis or progressive renal disease.

17. The method of claim 8, wherein the pulmonary fibrosis is diffuse interstitial pulmonary fibrosis.

18. The method of claim 8, wherein the acute fibrosis is in response to various forms of trauma including accidental injuries, infections, surgery, burns, radiation or chemotherapy treatments.

19. The method of claim 1, wherein the VEGFR1 signalling activity is mediated by one or both of AKT or PI3 kinase.

20. The method of claim 1, wherein inhibiting the VEGFR1 signalling activity decreases a connective tissue growth factor (CTGF) activity.

21. The method of claim 8, wherein the VEGFR1 signalling activity is mediated by one or mere both of AKT or PI3 kinase.

22. The method of claim 8, wherein inhibiting the VEGFR1 signalling activity decreases a connective tissue growth factor (CTGF) activity.

23. The method of claim 1 wherein the scleroderma is morphea, generalized morphea,, or linear scleroderma.

24. The method of claim 1 wherein the kidney fibrosis is glomerular sclerosis or renal tubulointerstitial fibrosis or progressive renal disease.

25. The method of claim 1 wherein the pulmonary fibrosis is diffuse interstitial pulmonary fibrosis.

26. The method of claim 1 wherein the acute fibrosis is in response to various forms of trauma including accidental injuries, infections, surgery, burns, radiation or chemotherapy treatments.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
agggcctctt ctgtgacttc g                     21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tcatgccatg tctccgtaca tc                    22